(12) United States Patent
Fliermans

(10) Patent No.: US 7,160,715 B2
(45) Date of Patent: Jan. 9, 2007

(54) RADIATION-RESISTANT MICROORGANISM

(75) Inventor: Carl B. Fliermans, Augusta, GA (US)

(73) Assignee: Westinghouse Savannah River Company LLC, Aiken, SC (US)

( * ) Notice: Subject to any disclaimer, the term of this patent is extended or adjusted under 35 U.S.C. 154(b) by 445 days.

(21) Appl. No.: 10/427,075

(22) Filed: Apr. 30, 2003

(65) Prior Publication Data

US 2003/0203476 A1    Oct. 30, 2003

Related U.S. Application Data

(60) Provisional application No. 60/376,646, filed on Apr. 30, 2002.

(51) Int. Cl.
    *C12S 1/00*     (2006.01)
    *C12N 1/20*    (2006.01)
(52) U.S. Cl. ................ 435/262.5; 435/252.4
(58) Field of Classification Search ........... 435/252.4, 435/262.5
    See application file for complete search history.

(56) References Cited

U.S. PATENT DOCUMENTS 5,401,398 A    3/1995    McManus ............ 210/150
5,922,204 A    7/1999    Hunter et al. ........... 210/603
5,954,858 A    9/1999    Peretti et al. ............. 95/44

OTHER PUBLICATIONS

Yokota et al 1993.International Journal of Systematic Bacteriology, vol. 43, No. 1, pp. 52-57.*
Hamana, K. 1994. Journal of General and Applied Microbiology, vol. 40, pp. 181-195.*
Frazier, M. & Johnson, G., Innovative Appraoches for Cleaning Up and Treating Hazardous Wastes at DOE Sites, Office of Science, U.S. Department of Energy, Washington, DC, undated.
Phillips et al., Kineococcus radiotolerans sp. nov., a radiation-resistant, Gram-positive bacterium, International Journal of Systematic and Evolutionary Microbiology (2002) 52, 933-938, Great Britain.

* cited by examiner

*Primary Examiner*—Jon Weber
*Assistant Examiner*—Kailash C. Srivastava
(74) *Attorney, Agent, or Firm*—J. Bennett Mullinax, LLC

(57) ABSTRACT

An isolated and purified bacterium is provided which was isolated from a high-level radioactive waste site of mixed waste. The isolate has the ability to degrade a wide variety of organic contaminants while demonstrating high tolerance to ionizing radiation. The organism is uniquely suited to bioremediation of a variety or organic contaminants while in the presence of ionizing radiation.

7 Claims, 3 Drawing Sheets

RADIATION-RESISTANT MICROORGANISM

RELATED APPLICATIONS

This application claims the benefit of U.S. application Ser. No. 60/376,646, filed on Apr. 30, 2002, and which is incorporated herein by reference.

STATEMENT AS TO RIGHTS TO INVENTIONS UNDER FEDERALLY-SPONSORED RESEARCH AND DEVELOPMENT

The U.S. Government has rights in this invention pursuant to Contract No. DE AC09-96SR18500 between Westinghouse Savannah River Company and the U.S. Department of Energy.

FIELD OF THE INVENTION

This invention is directed towards a novel, radiation-resistant, Gram-positive bacterium isolated from high-level radioactive, mixed waste storage materials. This invention is further directed to a process of using the isolated bacterium to treat high-level mixed waste so as to render the waste material into a less hazardous treated waste product.

BACKGROUND OF THE INVENTION

This invention relates to the identification and use of Extremophiles which, as used herein, include microbial communities which are adapted to extreme environments. Extreme environments may include high temperatures, low or high pH values, high pressures, desiccation stress, exposure to harsh chemicals, exposure to radiation, and combinations of environmental extremes.

Liquid high-level radioactive waste presents one of the most extreme environments known to man and ecological challenges with respect to adaptation of organisms to live in such an environment. The high-level radioactive waste tanks exhibit a number of extreme parameters with which microorganisms must deal. The environmental extremes include the elevation of temperature, salt, pH, organic constituents, inorganic constituents, and ionizing radiation. Any one of these parameters in the extreme are often sufficient to restrict life. Organisms which do adapt to such conditions have developed unique enzymatic pathways and other chemical and morphological adaptations which permit their survival. Such organisms and their adaptations are of interest.

SUMMARY OF THE INVENTION

It is one aspect of at least one of the present embodiments to provide for a bacterium which can grow at temperatures of between about 11° C. and about 41° C., operate in a pH range of between about 5 to about 9 and at NaCl concentrations up to and including about 5% weight/volume. Further, the organism is able to grow in high radiation environments having radiation levels which exceed 10 Gy h$^{-1}$ and may be as high as 100 Gy h$^{-1}$ or greater.

It is yet another aspect of at least one of the present embodiments to provide a novel bacterium which is capable of surviving in extreme environments which have new and useful enzymes which are operative within the extreme environment. Such enzymes provide an ability to metabolize organic waste while subject to extreme environmental conditions of heat, salt, pH, and ionizing radiation.

It is yet another aspect of at least one of the of the present embodiments of the invention to provide a novel bacterium capable of surviving in an extreme ionizing radiation environment and which is useful in the sequestration of radionuclides, cations, and heavy metals found within radioactive waste and mixed waste.

It is yet another aspect of at least one of the embodiments of the present invention to provide an isolated, purified culture of a bacterial organism which has the ability to degrade volatile organic contaminants in the presence of high levels of ionizing radiation.

These and other features, aspects, and advantages of the present invention will become better understood with reference to the following description.

DESCRIPTION OF THE PREFERRED EMBODIMENT

Figure 1:
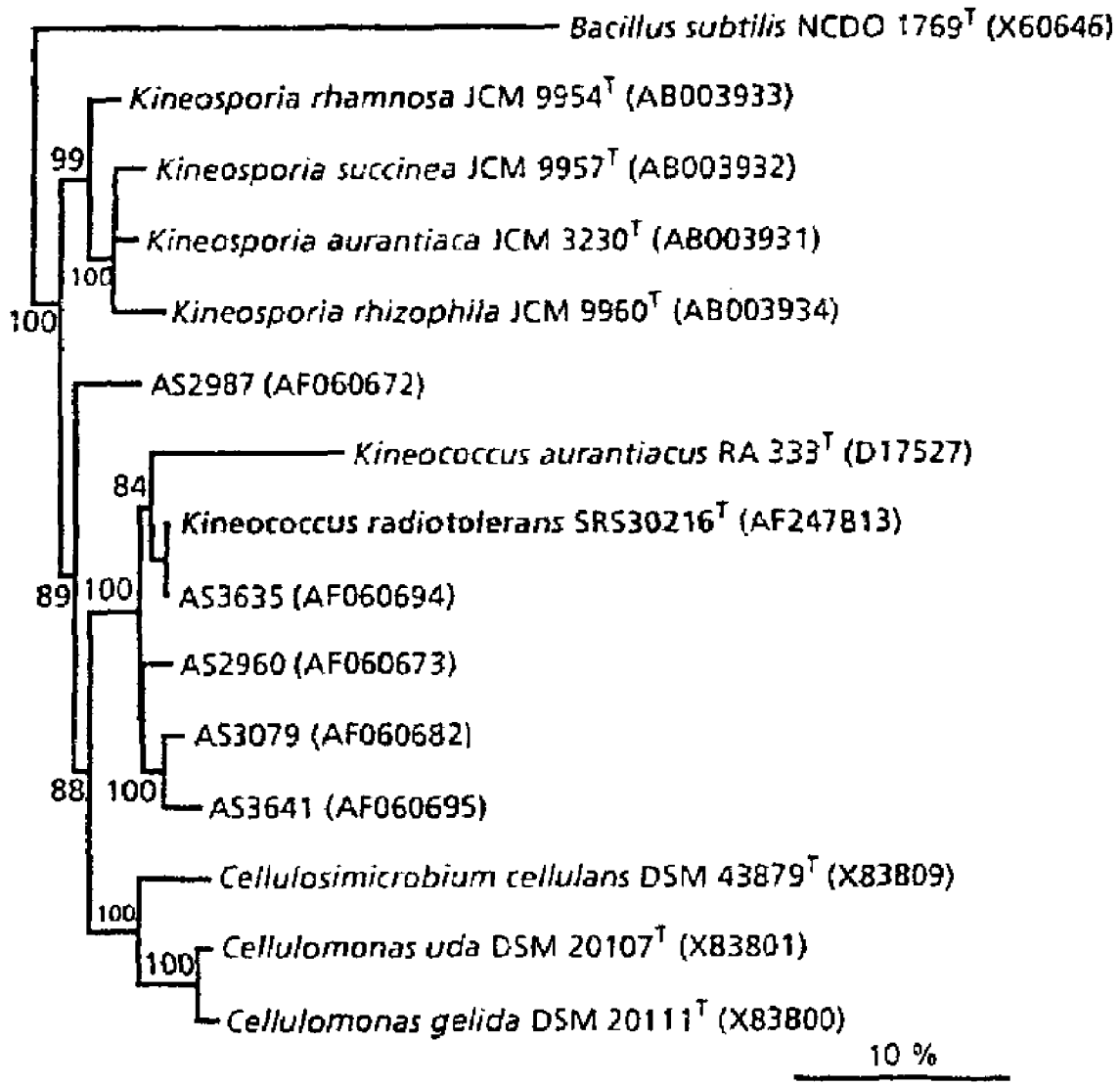
FIG. 1 is a phylogenetic tree setting forth the position and relationship of strain SRS30216 along with accession numbers for comparative organisms.

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

A bacterial isolate, strain SRS30216, was isolated from a high-level radioactive waste storage basin. The strain SRS30216 was isolated from a work area of a shielded cell facility associated with a high-level radiation waste storage basin. Details of the organism and isolation procedures may be found in reference to a publication co-authored by the inventor entitled "*Kineococcus radiotolerans* sp. nov., a radiation-resistant, Gram-positive bacterium", *International J. of Systemic and Evolutionary Microbiology*, Vol. 52, pp 933–938, May, 2002, and which is incorporated herein by reference. The high-level radiation storage basin is a mixed waste facility containing organic contaminants and high-level radioactive waste. γ-radiation levels within the basin may be as high as 100 Gy h$^{-1}$ (1 G=100 rads) and routinely exceeds 10 Gy h$^{-1}$.

Within the high-level mixed waste storage basins it has been observed that materials consistent with a bio-film were present within the waste tanks. Subsequent sampling and microscope examination of the tank contents revealed that bacterial colonies were present within the waste tank environment. In particular, high biological activity was noted at a foam-forming interface between the liquid contents and the vapor headspace within the enclosed tank. Additional evidence of biological activity is inferred from the corrosion or pitting of the carbon steel tanks in the region associated with the bio-film/foam interface.

Samples collected from high-level waste tanks were analyzed for the presence of DNA. Positive DNA samples were detected in 21% of the samples. The collected DNA has been amplified using universal forward and reverse primers 27F and 1392R, respectively, and the amplified 16S genes were cloned and sequenced. Sequence analysis suggested at least seven taxinomically different groups of bacterial 16S genes were present.

The designated strain SRS30216, was isolated from a shielded cell facility in the Savannah River Technology Center at the Savannah River Site. The isolation techniques were performed inside shielded cells and carried out using mechanical remote manipulators. A plastic-lined, paper-wrapped sterile swab was moved into the shielded cell and opened using remote manipulators. The swab was used to wipe the metal surface on the floor of the work area, the entire swab then being placed in a 10 ml PTYG nutrient solution contained in a 15 ml centrifuge tube. The nutrient solution has a formulation of 1% (w/v) glucose, 0.5% (w/v) yeast extract, 0.5% (w/v) tryptone, 0.5% (w/v) peptone, 0.006% (w/v) MgSO$_4$7H$_2$O, 0.0006% (w/v) CaCl$_2$, pH 10.7. The alkaline pH was chosen to reflect the alkaline nature of the radioactive samples normally processed in the work area. The sample was stored vertically without agitation for 145 days and then used to innoculate BIOLOG™ GN plates. After 29 days, the BIOLOG™ plate containing strain SRS30216 had four positive wells corresponding to L-arabinose, D-arabitol, cellobiose, and D-serine. Solutions from these four wells were plated on PTYG medium (pH 7.2) and an orange-pigmented microorganism was isolated and given the above designation. The type and only strain SRS 30216 is on deposit and available through American Type Culture Collection (ATCC), Manassas, Va., and Deutsch Sammlung Von Microorganimen Und Zelikulturen GmbH (DSM), MascheroderWeg 1b, D-38124 Braunschweig, Germany. The ATCC accession number is BAA-149, and the corresponding DSM-accession number is DSM-14245.

Following isolation and characterization of strain SRS30216 as set forth below, it has been determined that DNA material isolated directly from sampled high level waste tanks matches the DNA from the isolate that is believed to have originated from within the waste tank environment. Further, additional DNA material which does not match strain SRS30216 has been found within the waste tanks. Accordingly, Applicant believes additional bacteria isolates may be derived from the waste tanks, the additional isolates having useful remediation properties in both pure cultures along with mixed cultures with SRS30216.

Phylogenetic Analysis

Genomic DNA from strain SRS30216 was isolated utilizing the CTAB/NaCl procedure set forth in Meade et al, *Journal of Bacteriology*, 149:114–122, 1982, and which is incorporated herein by reference. The 16S rRNA gene of strain SRS30216 was amplified using the universal primers 27F (5'-AGAGTTTGATCMTGGCTCAG-3'; M=C/A) and 1392R (5'-ACGGGCGGTGTGTRC-3'; R=A/G) for the bacterial 16S rRNA gene (Wise et al, 1997) Both strands of the PCR product were sequenced (Molecular Genetics Instrumentation Facility, UGA, USA). The BLAST algorithm (Altschul et al, *Journal of Molecular Biology*, 215, 403–410, 1990, incorporated herein by reference) was used to identify the closest 16S rRNA gene matches present in GenBank. The closest relative of strain SRS30216 is the type and only validly published species of the genus *Kineococcus*, *Kineococcus aurantiacus* RA333$^T$ (Yokota et al, *International Journal of Systemic Bacteriology*, 43:52–57, 1993, and which is incorporated herein by reference). The type strain of *K. aurantiacus*, a motile, coccus-shaped bacterium, was isolated from soil from the Indore region of India. Comparison of the 16S rRNA genes of strain SRS30216 and *K. aurantiacus* RA 333 utiliizing the GAP program (GCG, Wisconsin Package) showed 93% similarity over 1268 bp internal to the 16S rRNA gene. A higher level of similarity, >97%, was observed between the 16S rRNA gene of strain SRS30216 and the 16S rRNA genes of uncharacterized and not validly published Mojave Desert isolates AS3635, AS2960, AS3641, AS3079, and AS2987, whose sequences are also available in GenBank (accession numbers AF060694, AF060673, AF060695, AF060682, and AF060672, respectively). The GenBank Accession No. for the 16S rRNA gene sequence of *Kineococcus radiotolerans* SRS30216 is AF247813.

A 1268 bp internal region of the amplified 16S rRNA gene sequence was used to perform phylogenetic analysis using PHYLIP version 3.5c (Felsenstein, Department of Genetics, University of Washington, Seattle, Wash. USA, 1993, incorporated herein by reference). Trees were constructed using the DNA distance and DNA parsimony methods (Hillis et al, *Molecular Evolution: Producing the Biochemical Data*, pp. 456–487, 1993, incorporated herein by reference). Bootstrap analyses for 100 resamplings were performed with both algorithms to provide confidence estimates for tree topologies (Felsenstein, *Evolution*, 39:783–791, 1985, incorporated herein by reference). 16S rDNA sequences from closely associated organisms, based on sequence similarity determined by the BLAST algorithm, were included in the analysis. Phylogenetic trees constructed by DNA distance (FIG. 1) and DNA parsimony (data not shown) demonstrate that strain SRS30216 and some of the uncharacterized bacteria from the Mojave Desert, such as AS3635, are more closely related to each other than to the type strain of *K. aurantiacus*. The tree set forth in FIG. 1 was constructed using the FITCH algorithm from a matrix of pairwise genetic distances as calculated by the Jukes-Cantor method. A total of 1,250 aligned positions was used in the analysis. The reference bar is indicative of 0.10 substitutions per base position. The numbers at the nodes of the tree indicate the number of times the group consisting of the species listed to the right of that fork occurred among 100 bootstrapped resamplings. Values below 60 are not shown. The accession number for each organism is given in parentheses. However, none of these strains were available for comparison.

DNA-DNA hybridization between strain SRS30216 and the type strain of *K. aurantiacus* was performed at the Deutsch Sammiung von Mikrooganismen und Zelikulturen GmbH, Braunschweig, Germany. The hybridization conditions used were described by De Ley et al (*European Jouranl of Biochemistry*, 12:133–142, 1970 and which is incorporated herein by reference), with the modifications described by Hub et al (*System of Applied Microbiology*, 4:184–192, 1983, and which is incorporated herein by reference) and Escara & Hutton (*Biopolymers*, 19:1315–1327, 1980, and which is incorporated herein by reference). DNA-DNA hybridization analysis between strain SRS30216 and strain RA 333 revealed only 31% similarity.

Morphological and Cultural Characteristics

Figure 2A:
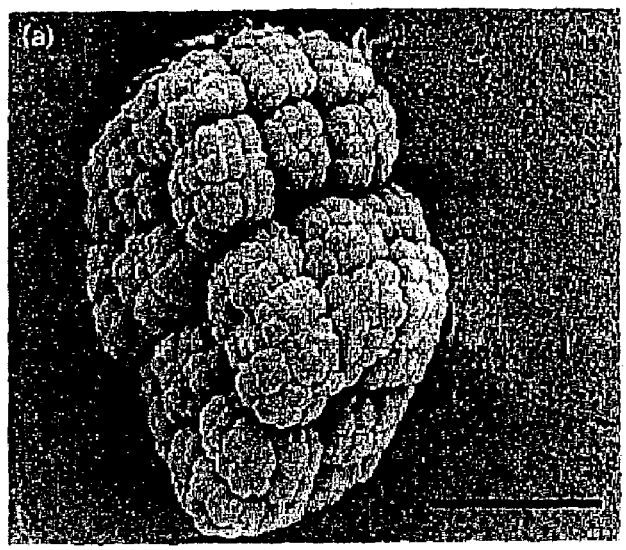
FIG. 2A is a scanning electron micrograph of isolate SRS30216 following culturing on PTYG agar.
Figure 2B:
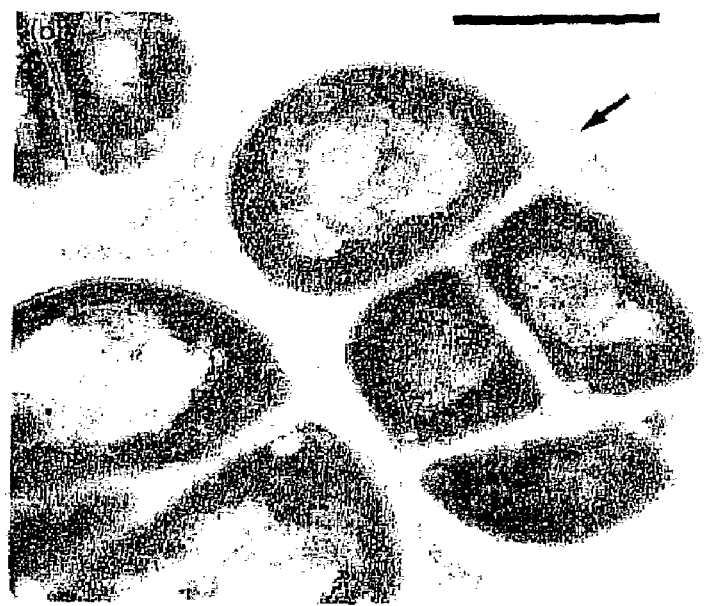
FIG. 2B is a transmission electron micrograph of a thin section of cells of strain SRS30216. The arrow indicates the presence of an extra-cellular matrix.

Strain SRS30216 colonies were orange and round with rough edges. Individual cells were coccus shaped, approximately 1.0–1.5 µm in diameter. Within a broth culture, approximately 1% of the cells were observed to be motile. Motility was stimulated in broth culture by incubation of cells in a solution of 10% sandy loam soil extract for 1 hour; in this case, the number of motile cells increased to nearly 100%. Motility was also observed as spreading colonies on yeast extract/malt extract plates [0.4% (w/v) yeast extract, 1% (w/v) malt extract, 0.4% (w/v) glucose, 0.3% (w/v) Bacto agar] incubated at 32° C. for 3 days. Scanning electron microscopy was performed to visualize cell morphology and flagella production. For cell morphology, cells were collected from broth cultures by centrifugation or scraped from a plate, washed once in 67 mM phosphate buffer (4.73 g $Na_2HPO_4 l^{-1}$, 4.5 g $KH_2PO_4 l^{-1}$, pH 7.0) and resuspended in 100 µl of the same buffer. An equal volume of 4% (v/v) glutaraldehyde in 0.1 M cacodylate buffer was added to the cell suspension for 1 hour at room temperature. The cells were then washed three times with phosphate buffer and collected on nitrocellulose filters with a 1 µm pore size (Millipore) before being serially dehydrated with ethanol using 20, 40, 60 and 80% (v/v) steps ending in three changes at 100%. Critical-point drying (Samdri) of the samples was performed before coating with chromium using a vacuum evaporator (Edwards) and observation with a LEO 982 field emission scanning electron microscope. When grown on plates or in broth, the cells grew in symmetrical clumps (FIG. 2a). For transmission electron microscopy, glutaraldehyde-fixed cells were embedded with Epon resin (Electron Microscopy Science) and polymerized at 60° C. for 18 hours. Seventy to eighty micrometre sections were cut with an RMC 6000 ultramicrotome (Ventana Medical Instruments) and viewed on a JEOL 100CX electronic microscope operating at 80 kV. Thin sections revealed clumps of cells surrounded by an extracellular matrix or slime layer (FIG. 2b). This cell-surface component was more apparent when cells were grown in broth (data not shown). Cells containing flagella were visualized by scanning electron microscopy using cells previously incubated in soil extract to induce motility before fixing with glutaraldehyde. Motile cells were more spherical than cells that were part of clusters (FIG. 2c).

Both strain SRS30216 and *K. aurantiacus* RA 333 produced an orange pigment that is soluble in methanol, thus allowing comparison of the pigments by absorption spectrum. Cultures of both strains were washed once with $H_2O$, resuspended in 100% methanol and vortexed vigorously for 5 minutes. After centrifugation at 12,000 g for 5 minutes, the methanol extract was removed and the visible light absorption spectrum was obtained from 340 to 600 nm using a Beckman DU640B spectrometer. Both pigment extracts contained absorption peaks at approximately 444, 471 and 501 nm, suggesting a carotenoid.

Physiological Characterization

Like *K. aurantiacus* RA 333, strain SRS30216 stained Gram-positive. Catalase activity was observed when a solution of 3% (v/v) hydrogen peroxide was dropped onto cells placed on a glass slide. No oxidase activity was seen in an assay involving reduction of 1% tetramethyl-p-phenylenediamine previously placed on filter paper disks. Unlike *K. aurantiacus* RA 333, however, urease activity was not observed on a urease slant. The temperature range for growth was determined in PTYG broth in a temperature gradient incubator set with low and high temperatures of 0 and 55° C. A growing culture of strain SRS30216 was diluted into fresh medium to an $OD_{600}$ of less than 0.1. A tenfold increase in optical density was considered positive for growth. Observation of cultures over 96 hours revealed growth in PTYG broth over a temperature range of 11° C. to 41° C. The doubling time at 32° C. was 2.5 hours. These characteristics are comparable to those of *K. aurantiacus* RA 333.

For pH range and salt tolerance experiments, exponential phase cells were diluted 1:500 into the appropriate medium and incubated at 32° C. A doubling of cell mass over the course of 3 days was considered positive. To determine the range of pH that would allow growth of strain SRS30216, cells were incubated in PTYG broth at a specific pH at 32° C. with aeration. The pH of the medium was measured both before and after growth to ensure that the pH had been maintained. As with *K. aurantiacus* RA 333, growth of strain SRS30216 was observed between pH 5 and 9, but not at pH 4.5 or 9.5 in PTYG. Growth in the presence of salt was determined by the addition of NaCl to PTYG broth to produce a series of concentrations from 0 to 7% (w/v) in 0.5% increments. Growth was observed at salt concentrations up to and including 5%. To determine the ability of the organism to use different carbon sources, cells were scraped from PTYG plates and resuspended in 0.5% (w/v) yeast extract. Different carbon sources were added at 0.5% (w/v) and the cultures were incubated for 3 days. Utilization of the carbon source was deemed positive if the cell density was at least double the density of the control culture, which contained no added carbon source. Strain SRS30216 utilized glucose, galactose, L-arabinose, sucrose, mannose, xylose, glycerol, mannitol, inositol and sorbitol as carbon sources. Rafinose, rhamnose, lactose, ribose and maltose were unable to stimulate growth. The Simmons citrate test was negative. Strain SRS30216 was unable to utilize ribose and citrate, thus differentiating it from *K. aurantiacus* RA333.

Additional profiling of strain SRS30216 was carried out using basal salt media in which various hazardous wastes were present to determine if the compounds could be metabolized by the bacterial strain. The evaluation technique, as well known within the art, consists of using a basal salt medium in which the indicated organic compound was added as the sole carbon source. (See Gordon, R. W., et al, *Use of Biolog™ Technology for Hazardous Chemical Screening, Microbiological Techniques*, 18:329–347, 1993 and which is incorporated herein by reference.) Enzymatic indicators such as tetrazolium chloride may be added to the agar substrate. Visible zones appearing around transferred isolates indicate enzymatic activity and, hence, metabolism of the indicated carbon source.

The basic procedures described here use Biolog™ GN (Biolog, Inc., Haywood, Calif.) plates which contain minimal nutritional factors along with various individual organic substrates in each of the 95 wells in a microtiter plate. *Kineococcus* SRS30216 isolates were inoculated into each microtiter plate well. The plates were incubated at 30° C. for 3 weeks, and the color changes indicative of the characteristic metabolic patterns were recorded. The 95 different carbon sources in Biolog™ GN and GP plates were preselected specifically for characterizing and differentiating Gram-negative and Gram-positive aerobic bacteria, respectively. They were useful in demonstrating metabolic patterns for mixed *Kineococcus* cultures. Carbon sources in the Biolog™ plates are dominated by 28 carbohydrates, 24 carboxylic acids, and 20 amino acids plus various amides, aromatic chemicals, as described in the Biolog™ literature.

Patterns that develop on Biolog™ microplates are a result of the oxidation of the substrates by *Kineococcus* in the inoculum and the subsequent reduction of the tetrazolium dye to form a color in response to detectable reactions. Depending upon the functional enzymes present in the isolate or community, one of a possible $4 \times 10^{28}$ patterns can be expressed. The patterns are distinctive for isolates of different species and are now being used to distinguish the physiological ecology of various microbial communities.

Biolog™ technology offers a unique capacity to measure functional aspects of bacterial enzyme activity in a reproducible and quantifiable way. Biolog™ plate patterns develop due to enzyme activity in each positive well. The enzyme activity of pure cultures enables the identification of the isolates based on the phenological patterns.

Biolog™ technology is the basic component of the rapid screening procedure and is predicated on tetrazolium dye reduction as an indicator of enzyme systems capable of sole carbon source utilization. While the technology does not depend on the isolation of the microorganisms, it does require a physiological response in order to provide a recordable signal. To achieve such a signal, the organisms must respond by using the organic substrates as electron donors to the tetrazolium chloride for the subsequent formation and deposition of formazan within the microbial cell. This transformation requires that the microorganisms supply enzymes capable of transporting and respiring the particular compound. The utilization of these compounds indicates that the microbial systems are capable of utilizing the compound under the experimental conditions. The use of the Biolog™ technology provides a rapid means for evaluating the autecological response of the microbial isolate, specific details for isolate SRS30216 being given below.

The compounds identified in Table 1 are degradable by the strain SRS30216.

TABLE 1

Aromatic Amines
Benzene
Biphenyl
Diphenylamine
Organic carbon
Phenol
Polycyclic Aromatics
Tetraphenyborate Additionally, set forth in Table 2 are additional organic sources that strain SRS30216 is able to utilize and degrade.

TABLE 2 carbohydrates
carboxylic acids
amino acids
alcohols
nucleotides
oligosaccharides
arbutin
tween 40 & 80
serine
cellobiose
fructose
maltose
psicose TABLE 2-continued glucose
acetate
pyruvate
malate
propionate
2,3,butandiol
uradine monophosphate Biochemical Analysis Fatty acid analysis was performed by Microbial ID based on GC column retention time using extracts from cells grown on TSBA [3% (w/v) tryptic soy broth with 1.5% (w/v) Bacto agar] at 30° C. With both strains, the majority of fatty acis (>90%) consisted of anteiso 15:0. This is similar to the value of 88.7% reported for *K. aurantiacus* RA 333 by Yokota et al, (*International Journal of Systemic Bacteriology* 43:52–27, 1993, incorporated herein by reference.). The remaining fatty acids had chain lengths between 14 and 18 and were found in similar percentages in strain SRS302167 and *K. aurantiacus* RA 333 (data not shown). Surprisingly, the results suggested that strain SRS30216 produced the α-polyunsaturated fatty acid 20:4ω6,9,12,15c (arachidonic acid). The identification of polyunsaturated fatty acids produced by bacteria has been limited to organisms isolated from marine psychrophilic environments. A closer examination of the lipid and fatty acid composition of strain SRS30216 was undertaken using MS at the Center for Biomarker Analysis (Knoxville, Tenn., USA). Cells were grown in PTYG broth at 15° C., 23° C., and 37° C. and the lipids were extracted after purification from lyophilized cells. The lipids were fractionated into polar, neutral and glycolipids by sequential elution from a silicic acid column. Fatty acid methyl esters were identified by GC-MS of samples using a Hewlett Packard 6890 series GC interfaced to a Hewlett Packard 5973 mass selective detector. Again, the vast majority of the fatty acids were anteiso 15:0, regardless of the chemical nature of the lipid (polar, neutral, or glycolipid) or growth temperature. Arachidonic acid was not detected and the peak corresponding to it in the MIDI analysis was probably an alkene. Interestingly, when strain SRS30216 was grown at 15° C., no neutral lipids were produced; instead, this fraction was composed entirely of alkenes. Alkenes were produced at all three temperatures and were composed of a variety of species with chain lengths of 19 to 24 carbons. One alkene containing 21 carbons and one alkene containing 22 carbons together constituted approximately 70% of the total alkene production. The exact nature of these compounds has not been investigated.

Radiation Resistance

Figure 3:
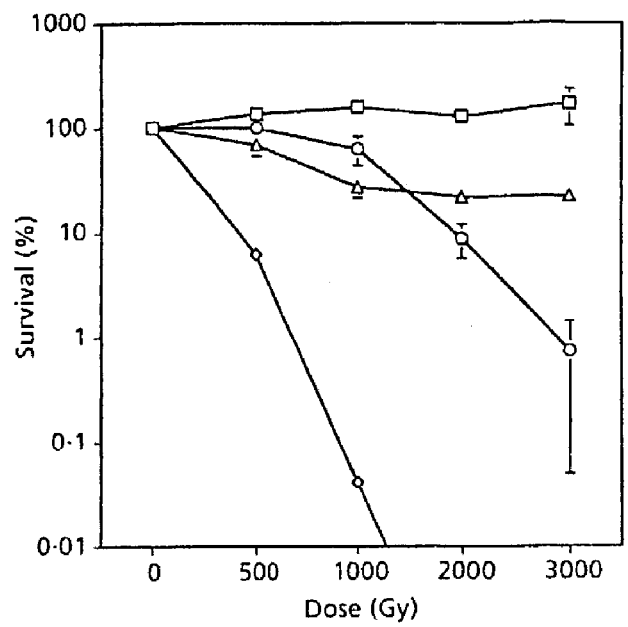
FIG. 3 is a graph setting forth resistance to gamma-radiation from a $^{60}$Co source comparing radiation resistance of SRS30216 to other bacteria.

Since strain SRS30216 was isolated from a radioactive work area, the radiation resistance of this strain was compared to that of *K. aurantiacus* RA 333 and the radiation-resistant organism *Deinococcus radiodurans* ATCC 13939. Exponentially growing cultures of *D. radiodurans* ATCC 13939, *Escherichia coli* CF1648 (recA$^+$) [obtained from M. Cashel (NIH, Bethesda, Md., USA) and used as a radiation-sensitive control], strain SRS30216 and *K. aurantiacus* RA 333 were washed and resuspended in an equal volum of 67 mM phosphate buffer and divided into 100 μl aliquots. The cell suspensions were exposed to a $^{60}$Co source for predetermined times. At each time-point, three individual aliquots of each strain were removed from the radiation source. Cell suspensions were serial diluted in 67 mM phosphate buffer and plated on PTYG medium. After 3 days growth, colony forming units (c.f.u.) were counted and the percentage survival was calculated based upon the number of c.f.u. present before irradiation. *K. aurantiacus* RA333 showed an intermediate level of radiation resistance compared with *D. radiodurans* ATCC 13939 and *E. coli* CF1648, but was much less resistant than SRS30216 (FIG. 3). In fact, no logarithmic killing of strain SRS30216 was observed at doses up to 3.5 kGy and less than a 1 log difference was observed between strain SRS30216 and *D. radiodurans* ATCC 13939 at 3.5 kGy.

The waste tank environment from which the isolate SRS30216 was obtained routinely has radiation levels which exceed 10 Gy $h^{-1}$. More typically, radiation levels are between about 10 Gy $h^{-1}$ to 100 Gy $h^{-1}$. Further, not uncommonly, ionizing radiation levels may exceed 100 Gy $h^{-1}$ within the waste tank environment. The ability of the SRS30216 isolate to tolerate the indicated radiation levels affords an opportunity for the organisms to undergo bioremediation of indicated contaminants while in the presence of ionizing radiation levels which would typically preclude the use of conventional bioremediation organisms.

Further, it is noted that the isolate SRS30216 demonstrates a significant resistance to ionizing radiation levels and exhibits strong resistance to mutation. Accordingly, the enzymatic pathways and ligases of the isolate appear highly effective and accurate in bringing about the repair of damaged DNA. To the extent the isolate is resistant to mutations, such characteristic is useful in remediation protocols where high radiation levels may be present.

Desiccation Resistance

Figure 4:
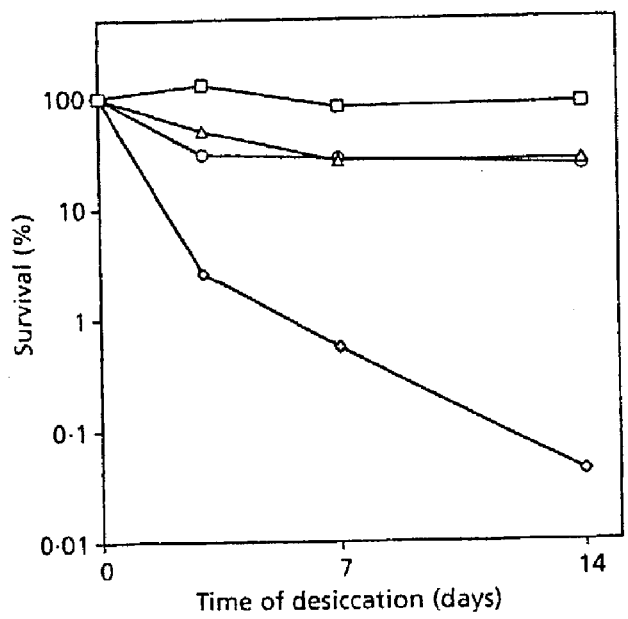
FIG. 4 is a graph setting forth data directed to desiccation resistance of SRS30216 in reference to comparative organisms.

Because a correlation has been made between desiccation resistance and radiation resistance, strain SRS30216 was tested for desiccation resistance. Exponentially growing cultures were washed once and resuspended in an equal volume of 67 mM phosphate buffer. Aliquots (1 ml) of cultures of *D. radiodurans* ATCC 13939, *E. coli*, strain SRS30216 and *K. aurantiacus* RA333 were placed onto glass cover-slips (1 inch×1 inch). The cover-slips were then placed in sterile Petri dishes inside a vacuum desiccator containing calcium sufate. An electronic hygrometer (Fisher Scientific) measured the humidity as 7±2% at 25° C. The percentage survival for each strain was determined at 3, 7, and 14 days after desiccation. At each time-point, one cover-slip containing each strain was removed. Phosphate buffer (1 ml) was added to the cover-slips to rehydrate the cells. Tenfold serial dilution and plating was then used to determine the percentage survival. Over a 2 week period, *D. radiodurans* ATCC 13939 showed the most resistance and *E. coli* CF1648 showed the least resistance. SRS30216 and RA333 were similar and only slightly less resistant than *D. radiodurans* ATCC 13939 (FIG. 4).

In conclusion, strain SRS30216 shows 93% 16S rDNA sequence identity to *K. aurantiacus* RA333. Furthermore, DNA-DNA hybridizaton experiments revealed only 31% DNA similarity between strain SRS30216 and *K. aurantiacus* RA 333. Strain SRS30216 was much more resistant to γ-radiation than *K. aurantiacus* RA 333. Although strain SRS30216 is very similar to *K. aurantiacus* RA333, it differs enough in 16S rDNA sequence and DNA similarity by DNA-DNA hybridization to be considered a separate species. The original description of *K. aurantiacus* RA 333 suggests that this genus should be included in the family Pseudonocardiaceae (Embley et al, *System of Applied Microbiology*, 11:44–52, 1988, incorporated herein by reference). One of the main properties of this family is the production of a majority of iso- and anteiso-branched chain fatty acids. The fatty acid composition of strain SRS30216 (mainly anteiso 15:0) is consistent with the inclusion of this organism in the family Pseudonocardiaceae. However, the proposed 16S rDNA signature sequence for Pseudonocardiaceae (Strackebrandt et al, *International Journal of Systemic Bacteriology*, 47:479–491, 1997, incorporated herein by reference) is not conserved in SRS30216, with differences at 12 of 20 positions (data not shown). *K. aurantiacus* RA333 also poorly matched the signature sequence.

In light of the above findings, it is proposed that the novel isolate be placed in the genus *Kineococcus* as a novel species, *Kineococcus radiotolerans* sp. nov. An overview of *Kineococcus radiotolerans* (ra.di.o.tó le.rans. L. n. radiatio radiation; L. part. adj. tolerans tolerating; N.L. adj. radiotolerans radiation-tolerating) is set forth below.

Identifying Characteristics

Cells are cocci, 1.0–1.5 μm in diameter. Cells occur in pairs, tetrads and in larger clusters. Colonies are circular, rough and orange-pigmented. Gram-reaction is positive. Cells are motile, produce polar flagella, and are catalase-positive. Urease and oxidase tests are negative. A variety of carbon sources are used including glucose, galactose, L-arabinose, sucrose, mannose, xylose, glycerol, mannitol, inositol and sorbitol, but not raffinose, rhamnose, lactose, citrate, ribose or maltose. The major fatty acid produced is anteiso 15:0 (approximately 90%). An orange pigment, soluble in methanol, with an absorption spectrum containing peaks at 444, 471, and 501 nm, is produced. The type and only strain is SRS30216 (=ATCC BAA-149$^T$=DSM 14245$^T$), which was isolated from the Savannah River Site in Aiken, S.C., USA.

The isolate SRS30216 has qualities and growth characteristics which make it ideally suited for treating mixed waste in ways and under conditions which were not previously available. As such, the organism is unique in its ability to metabolize certain contaminants as seen in reference to Table 1 and to do so in the presence of high levels of radiation, high temperature, high pH, and high saline environments. Heretofore, no organism having these combined abilities has been available for such remediation efforts. As such, the isolate SRS30216 may be used in bioreactors, biofilters, rotating biological contactors, and other gaseous and/or liquid bioreactors to treat liquid and gaseous waste while being exposed to high radiation levels.

For instance, rotating biological contactors (RBC) technology typically uses a fixed film or random, loose media upon which the bacteria isolate is allowed to colonize. In the process of colonization, the isolate forms a bio-film which provides a surface area upon which the resulting waste stream is exposed to the media-supporting bio-film. In a conventional RBC construction, the media may be formed of alternate layers of formed and flat sheets of polyethylene which may be thermally welded to produce a controlled, uniform spacing. The media is attached to a shaft through a hub assembly to achieve a final shape of the RBC in the form of a cylindrical drum. Alternatively, an RBC apparatus may utilize a random, loose media such as hemispherical pieces of polyethylene or propylene. One such RBC construction and operation may be seen in reference to U.S. Pat. No. 5,401,398 assigned to Geo-Form, Inc., and which is incorporated herein by reference. As indicated in the above cited reference, the media may be of various sizes and shapes so as to promote good adhesion of bacteria and the formation of a high bio-film surface area.

The use of a RBC is believed to be particularly useful in the treatment of hazardous mixed waste. The rotating bed which supports the media in the biomass functions much like a water wheel which contacts both a liquid component of the waste and a vapor component of the waste in a rotating manner. As such, the isolate used to colonize the media is exposed to metabolizable contaminants which are present in either the liquid or the vapor phase.

The rotating biological contactor may be used in situ within a mixed waste tank or housed in a separate container in which the hazardous mixed waste material is introduced into the bioreactor in either a continuous or batch phase process. The biotreatment process may continue until an adequate reduction in the organic contaminant of interest is achieved. It is envisioned that a plurality of bioreactors such as a rotating biological contactor may be used in series so as to achieve a more rapid and effective reduction of the organic contaminant of interest. Accordingly, the present isolate has the ability to treat contaminants present within the liquid phase of the waste when exposed to liquid within the RBC. Similarly, when the portion of the media and isolate is exposed to the vapor phase within the RBC, the treatment of benzene and other identified compounds will occur.

Alternatively, the *Kineococcus* isolate may be placed on a polycarbonate, polystyrene, or glass matrix as part of a conventional air stripping tower. As is well known within the art, air stripping towers allow for the formation of large, effective amounts of bio-film using a minimal amount of substrate material. The stripping tower can be used in conjunction with an upflow reactor where a gaseous material or liquid is loaded along the bottom of the reactor and discharged out the top. As is known within the bioremediation art, the treated off gas exiting the top of the tower may be recirculated by multiple passes through the reactor until an effective amount of the contaminant of interest is degraded or absorbed. The tolerance of the *Kineococcus* isolate to extreme conditions of pH, salinity, temperature, radiation, and multiple combinations of such environmental stresses afford the *Kineococcus* isolate the ability to remove and treat contaminants of waste streams which heretofore were believed incapable of direct biotreatment. To the extent other unique isolates exhibiting one or more useful properties of the present *Kineococcus* isolate strain may be found in other waste tank environments, it is believed that combinations of mixed cultures of such isolates with the present *Kineococcus* isolate may be useful in bioremediation techniques for high-level waste tank materials.

As seen in reference to FIG. 2A, the *Kineococcus* isolate exhibits a multi-clumping growth morphology which is unusual within the bacteriological domain. The multi-clumping growth morphology is beneficial in that it provides for a greater surface area. Additionally, it has been observed that the isolate produces unusually large amounts of polysaccharide biomass. (See FIG. 2B) The ability of the polysaccharide-containing cell wall/envelope of bacterium to accomplish bioaccumulation of cations from aqueous environments is well known. As first observed by G. C. Polikarpov, *Radioecology of Aquatic Organisms* (North Holland, N.Y., 1966) and which is incorporated herein by reference, microbial systems will accumulate radionuclides from a liquid environment. Such bioaccmulation occurs whether the bacterium is alive or dead and is accomplished through the ion exchange and absorption properties inherent in natural polysaccharides. Based upon the amount of produced polysaccharides of the *Kineococcus* isolate, it is expected that the isolate has an ability to bioabsorp metals, including radionuclides at levels in excess of 200 mg/gram of bacteria.

As such, the isolate has the ability to sequester cations, metals, and radionuclides which are present within the liquid phase of a mixed waste. While many metals and radioactive compounds have been precipitated by various treatment protocols, there remains radionuclides and other metals present within the liquid phase of the waste. As such, the organism lends itself well to the removal of such metals and radionuclides through the use of various biotreatment protocols referenced herein. Such biotreatment protocols may be adopted either primarily for the bioasorption of metals from the waste or, alternatively, as a useful parallel process which occurs in tandem with the bioremediation of organic waste.

The ability of the isolate to survive and grow during exposure to high radiation levels increases the innate ability of the organism to effectively bioremediate the indicated organic contaminants as well as accumulate various metals and radionuclides. Remediation in the presence of high radiation fields is key for the mixed hazardous wastes. Conventional organisms useful for bioremediation of organic waste would not tolerate the harsh conditions of radiation, pH, and salinity. The current isolate is able to survive under such conditions and may, therefore, provide effective treatment and bioremediation of contaminants and metals within the waste. In so doing, it is not necessary to first dilute or pretreat the hazardous mixed waste.

This ability to directly treat the unaltered hazardous mixed waste is important since any dilution, filtration, or additive-based pretreatment of the hazardous mixed waste merely adds to the volume of contaminated materials and/or structures. As such, the present organism fulfills a critical need within the area of bioremediation in terms of its ability to remain biologically active in the presence of radiation levels, pH, and salinity conditions, which either individually or in combination, heretofore were thought to preclude biological activity.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the claims of the present invention. In addition, it should be understood that aspects of the various embodiments may be interchanged, both in whole or in part. Therefore, the spirit and scope of the invention should not be limited to the description of the preferred versions contained therein.

That which is claimed:

1. An axenic culture of a microorganism having the ATCC accession number BAA-149, or a mutant thereof, wherein the mutant retains the property of metabolizing a compound selected from the group consisting of aromatic amines, benzene, biphenyl, diphenylamine, organic carbon, phenol, polycyclic aromatics, tetraphenylborate and combinations thereof.

2. A freeze-dried culture of the microorganism having the ATCC accession number BAA-149, or a mutant thereof, wherein the mutant retains the property of metabolizing a compound selected from the group consisting of aromatic amines, benzene, biphenyl, diphenylamine, organic carbon, phenol, polycyclic aromatics, tetraphenylborate and combinations thereof.

3. An isolated pure culture of a microorganism, ATCC BAA-149, or a mutant thereof, wherein said culture and the mutant thereof retain the property of metabolizing a compound selected from the group consisting of aromatic amines, benzene, biphenyl, diphenylamine, organic carbon, phenol, polycyclic aromatics, tetraphenylborate and combinations thereof.

4. A process for biodegradation of a material selected from the group consisting of aromatic amines, benzene, biphenyl, diphenylamine, organic carbon, phenol, polycyclic aromatics, tetraphenylborate and combinations thereof comprising cultivating a microorganism according to claim 1 in an aqueous medium having at least one of said contaminants, said medium further comprising a radioactive environment having radiation levels of at least about 10 Gy per hour.

5. A process for biodegradation of a material selected from the group consisting of aromatic amines, benzene, biphenyl, diphenylamine, organic carbon, phenol, polycyclic aromatics, tetraphenylborate and combinations thereof comprising cultivating a microorganism according to claim 3 in an aqueous medium having at least one of said contaminants, said medium further comprising a radioactive environment having radiation levels of at least about 10 Gy per hour.

6. A process of degrading a contaminant selected from the group consisting of aromatic amines, benzene, biphenyl, diphenylamine, organic carbon, phenol, polycyclic aromatics, tetraphenylborate, and combinations thereof in the presence of ionizing radiation levels of at least about 10 Gy per hour by contacting said contaminant with a microorganism according to claim 1.

7. A process of degrading a contaminant selected from the group consisting of aromatic amines, benzene, biphenyl, diphenylamine, organic carbon, phenol, polycyclic aromatics, tetraphenylborate, and combinations thereof in the presence of ionizing radiation levels of at least about 10 Gy per hour by contacting said contaminant with a microorganism according to claim 3.

* * * * *